United States Patent [19]

Grindstaff

[11] Patent Number: 5,083,450
[45] Date of Patent: Jan. 28, 1992

[54] GAS CHROMATOGRAPH-MASS SPECTROMETER (GC/MS) SYSTEM FOR QUANTITATIVE ANALYSIS OF REACTIVE CHEMICAL COMPOUNDS

[75] Inventor: Quirinus G. Grindstaff, Oak Ridge, Tenn.

[73] Assignee: Martin Marietta Energy Systems, Inc., Oak Ridge, Tenn.

[21] Appl. No.: 525,798

[22] Filed: May 18, 1990

[51] Int. Cl.$^5$ .............................................. G01N 30/72
[52] U.S. Cl. ....................................... 73/23.25; 73/23.37; 422/89
[58] Field of Search .................. 73/23.25, 23.37, 23.41; 250/288; 422/89

[56] References Cited

U.S. PATENT DOCUMENTS

| | | |
|---|---|---|
| 3,103,807 | 9/1963 | Broerman . |
| 3,198,001 | 8/1965 | Ferrin .................................. 73/23.25 |
| 3,301,482 | 1/1967 | Bullen ............................. 73/23.25 X |
| 3,305,000 | 2/1967 | Bullen et al. . |
| 3,327,520 | 6/1967 | Stapp, Jr. ....................... 73/23.25 X |
| 3,407,647 | 10/1968 | Lynn ................................. 73/23.25 |
| 3,418,513 | 12/1968 | Elliott . |
| 3,438,243 | 4/1969 | Parks, Jr. et al. . |
| 3,453,811 | 7/1969 | Crowley ............................... 55/386 |
| 3,507,147 | 4/1970 | Llewellyn . |
| 3,654,457 | 4/1972 | Yano et al. . |
| 3,695,011 | 10/1972 | Leech et al. ......................... 55/386 |
| 3,712,111 | 1/1973 | Llewellyn . |
| 3,723,729 | 3/1973 | Kruger et al. . |
| 3,773,964 | 11/1973 | Brady et al. . |
| 4,004,881 | 1/1977 | Ligon, Jr. . |
| 4,035,168 | 7/1977 | Jennings .......................... 55/197 X |
| 4,039,828 | 8/1977 | Pokar et al. ........................ 250/288 |
| 4,055,987 | 11/1977 | McFadden ....................... 73/61.1 C |
| 4,112,297 | 9/1978 | Miyagi et al. ..................... 250/288 |
| 4,160,161 | 7/1979 | Horton ............................... 250/281 |
| 4,176,542 | 12/1979 | Redding ........................... 73/23.25 |
| 4,213,326 | 7/1980 | Brodasky . |
| 4,251,725 | 2/1981 | Adkisson .......................... 250/281 |
| 4,253,026 | 2/1981 | Veach et al. ....................... 250/426 |
| 4,271,695 | 6/1981 | Sisti et al. . |
| 4,391,778 | 7/1983 | Andresen et al. ................... 422/89 |
| 4,420,679 | 12/1983 | Howe . |
| 4,531,056 | 7/1985 | Labowsky et al. ................ 250/288 |
| 4,559,063 | 12/1985 | Munari et al. .................... 55/386 X |
| 4,570,068 | 2/1986 | Sakairi et al. ..................... 250/288 |
| 4,587,835 | 5/1986 | Adams ............................. 73/23.37 |
| 4,641,541 | 2/1987 | Sharp ............................... 73/864.81 |
| 4,662,914 | 5/1987 | Hansen et al. ...................... 55/386 |
| 4,713,963 | 12/1987 | Sharp . |
| 4,730,111 | 3/1988 | Vestal et al. ...................... 250/288 |
| 4,732,581 | 3/1988 | Cheh et al. ........................... 55/67 |
| 4,734,107 | 3/1988 | Trestianu et al. ............... 55/386 X |
| 4,742,232 | 5/1988 | Biddle et al. ..................... 250/427 |
| 4,771,628 | 9/1988 | Sisti et al. . |
| 4,804,839 | 2/1989 | Broadbent et al. .............. 250/288 |
| 4,808,820 | 2/1989 | Blau ................................... 250/281 |
| 4,814,612 | 3/1989 | Vestal et al. ...................... 250/288 |
| 4,824,446 | 4/1989 | Mowery, Jr. .......................... 55/67 |
| 4,845,364 | 7/1989 | Alexander et al. ............. 250/288 X |
| 4,847,493 | 7/1989 | Sodal et al. ..................... 250/288 X |
| 4,853,539 | 8/1989 | Hall et al. .......................... 250/288 |
| 4,869,835 | 9/1989 | Ogawa et al. .................... 250/423 |
| 4,872,334 | 10/1989 | Watanabe . |
| 4,874,944 | 10/1989 | Kato .................................. 250/288 |
| 4,879,458 | 11/1989 | Brunfeldt et al. ................ 250/288 |
| 4,882,047 | 11/1989 | Shalon ............................. 210/198.2 |
| 4,883,957 | 11/1989 | Kinge et al. ...................... 250/283 |

Primary Examiner—Hezron E. Williams
Assistant Examiner—Joseph W. Roskos
Attorney, Agent, or Firm—George L. Craig; Ivan L. Ericson

[57] ABSTRACT

Described is a new gas chromatograph-mass spectrometer (GC/MS) system and method for quantitative analysis of reactive chemical compounds. All components of such a GC/MS system external to the oven of the gas chromatograph are programmably temperature controlled to operate at a volatilization temperature specific to the compound(s) sought to be separated and measured.

30 Claims, 5 Drawing Sheets

GAS CHROMATOGRAPH-MASS SPECTROMETER (GC/MS) SYSTEM FOR QUANTITATIVE ANALYSIS OF REACTIVE CHEMICAL COMPOUNDS

This invention was made with Government support under contract DE-AC05-84OR21400 awarded by the U.S. Department of Energy to Martin Marietta Energy Systems Inc. and the Government has certain rights in this invention.

BACKGROUND OF INVENTION

1. Field of Invention

This invention pertains to an apparatus and method for quantitatively measuring low levels of occurrence of certain compounds or substances. More particularly, the invention pertains to detecting and measuring occurrence of highly reactive compounds at levels in the parts per billion (ppb) and parts per trillion (ppt) range.

2. Description of Prior Art

A gas chromatograph (GC) is a powerful analytical device which takes fixed volumes of sample gases, or liquids which can be volatilized, and introduces these samples into a separation column which contains a stationary phase of adsorbent liquid material. The sample is then transported through the column by a mobile phase carrier gas. Individual molecules of the sample gas are adsorbed and then released at different times from the adsorbent stationary phase material in the column. By selection of the proper mobile and stationary phase materials and the temperature program of the GC, a sample containing a mixture of chemical compounds can be separated by the GC in such a way that only one compound will elute from the GC column at a time.

The liquid samples are introduced into the analytical column by two principle agencies: a heated injector (for example, a Grob split/splitless injector) or a cold-on-column injector. The eluting compounds taken from the GC analytical column can be detected by a variety of detectors. Typical detectors are electron capture detectors, electrolytic conductivity detectors, alkali flame ionization detectors, flame photometric detectors, thermal conductivity detectors, flame ionization detectors and mass spectrometers. For all the detectors except the mass spectrometer, the signal peaks generated by the detector indicating presence of specific compounds must be completely separated (resolved) for accurate quantitative analysis to be performed. The mass spectrometer can provide accurate quantitative analysis of co-eluting compounds by specific ion monitoring at a single mass number or simultaneous monitoring of the mass number of several selected fragment ions. The present invention involves a gas chromatograph/ mass spectrometer (GC/MS) system.

In a perfect GC/MS system, every molecule which is volatilized in the injector of the G is detected by the MS. However, because of reversible and nonreversible adsorption and thermal/catalytic decomposition of the volatilized compounds within conventional GC/MS systems, such efficiency is not achievable. This problem increases as the degree of reactivity of the compounds under analysis increases.

A large percentage of conventional GC/MS systems attempt to perform accurate analyses of reactive compounds and use a heated injector of the Grob split/splitless type. Because of the temperature at which they are operated and the internal construction of the injector, this heated injector causes thermal/catalytic decomposition of many highly reactive compounds as described above and is unsuitable for accurate analyses at very low concentrations of the compounds. The conventional high operating temperature of the injector (approximately 10° C. higher than the maximum temperature of the GC oven) creates active thermal sites within the internal elements of the injector and these thermally active sites subsequently induce catalytic and thermal decomposition and reversible/nonreversible adsorption of the reactive compounds under analysis. To prevent these adverse effects caused by maintaining the injector at such high temperatures, a few GC/MS systems use cold-on-column injectors. A conventional cold-on-column injector system consists of an injector body held at room temperature and a 1 to 5 meter length of deactivated fused silica column. The length of deactivated column is known as a precolumn and is used to prevent solvent flooding effects and contamination of the analytical column within the GC. In a conventional system the precolumn resides inside the GC oven and is coupled to the analytical column. However, when the GC oven is cycled from room temperature to approximately 300° C., the heating of the deactivated fused silica precolumn at temperatures exceeding 135° C. cause the precolumn to become thermally activated. The connection between the GC and the MS through an interface is also made with deactivated fused silica tubing which is subject to the same thermal activation problem since conventional systems require the interface also be operated at approximately 10° C. higher than the maximum temperature of the GC oven. Conventional GC/MS systems also require that the ion source of the mass spectrometer be operated at 10° C. higher than the maximum temperature of the GC oven. Under these conditions the metal ionization chamber of the MS also produce catalytic/ thermal decomposition and reversible/nonreversible adsorption of the compounds under analysis.

The present invention avoids these limitations of conventional GC/MS systems by preventing the chemical compounds under analysis, the surfaces of the injector system, the GC/MS interface and the ion source of the mass spectrometer from being subjected to high temperatures in excess of the volatilization temperature of the compound(s) under analysis which cause thermal decomposition and activation. The present invention is designed and operated such that the aforementioned components are operated at a temperature much lower than prescribed by conventional rules and which is programmably specific to the compound(s) under analysis.

SUMMARY OF INVENTION

The principle object of invention is to provide an apparatus and method for detecting and measuring compounds in a temperature controlled environment related to the volatility of the compound(s).

A further object of invention is to provide an apparatus and method for volatilizing, transporting and detecting reactive compound(s) without subjecting the compound(s) to heat exceeding that necessary to volatilize the compound(s).

Yet another object of invention is to provide an apparatus and method for detecting/measuring reactive compound(s).

The present invention accomplishes these and other objects of invention by providing a gas chromatography/ mass spectrometer (GC/MS) system for separation and measurement of volatilized compounds, said system comprising:

(a) a thermally isolated injector array for volatilizing and introducing said compounds into said gas chromatograph;

(b) a thermally isolated interface array for transporting said volatilized compounds from said gas chromatograph into an inert ionization chamber of said mass spectrometer; and (c) programmable temperature control means coupled to said injector array, said interface array and said mass spectrometer to selectively control a volatilization temperature of said compounds while in said injector array, interface array and mass spectrometer.

The present invention also accomplishes the above and other objects of invention by providing a method of operating a gas chromatograph/mass spectrometer system for separation and measurement of a molecular compound, said method comprising the steps of:

(a) introducing a test sample containing said compound into an injector array;

(b) programmably heating said test sample within said injector array to a volatilization temperature specific to said compound;

(c) thermally isolating said injector array from said gas chromatograph;

(d) introducing said test sample into said gas chromatograph;

(e) operating said gas chromatograph in such a manner as to separate all compounds in said test sample;

(f) transmitting said separated compounds to an inert ionization chamber of said mass spectrometer via an interface array thermally isolated from said gas chromatograph and said mass spectrometer;

(g) programmably maintaining said interface array and said ionization chamber at said volatilization temperature specific to said compound; and (h) measuring mass to charge ratios specific to said particular compound with said mass spectrometer.

DESCRIPTION OF THE PREFERRED EMBODIMENT

Figure 1:
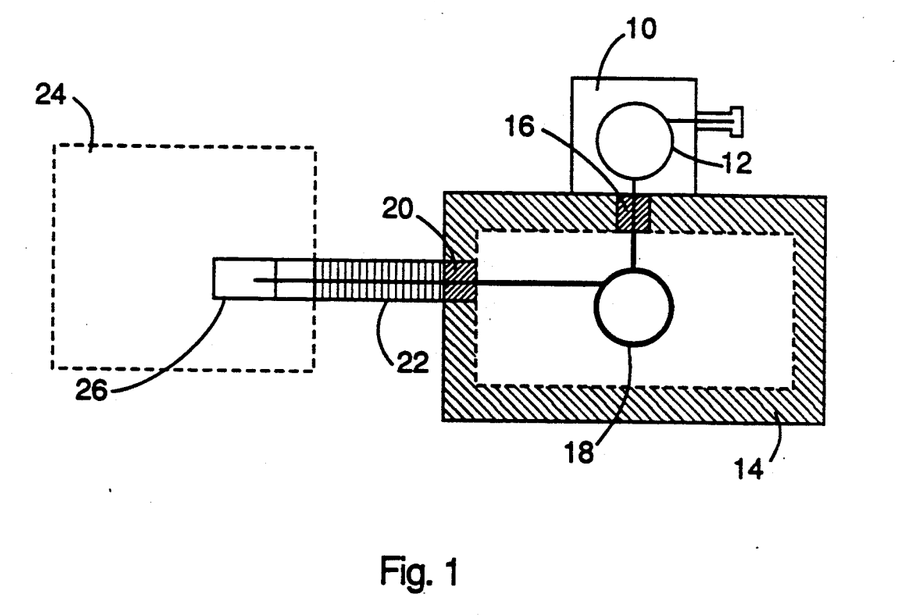
FIG. 1 is a general schematic drawing of a separation/measurement apparatus made according to the present invention.

FIG. 1 is a schematic of the basic components of a GC/MS system constructed according to the invention. An on-column injector array 10 containing a pre-column 12 for volatilizing and transporting to the analytical column of the GC a sample of a substance to be analyzed is located external to the oven 14 of the gas chromatograph (not shown) and is thermally isolated from the oven 14 by an insulating interface plate 16. The pre-column 12 joins an analytical column 18 contained in the GC oven 14. After thermally cycling the GC oven, the separated compounds of the sample from the analytical column 18 are transported through a second insulating interface plate 20 to a temperature programmable interface array 22 thermally isolated from the gas chromatograph and the mass spectrometer. The separated compounds are then transported via a second deactivated fused silica column 48 within the interface array which is connected to the analytical column 18 into a programmably temperature-controlled ionization chamber 26 of the mass spectrometer 24.

Figure 2:
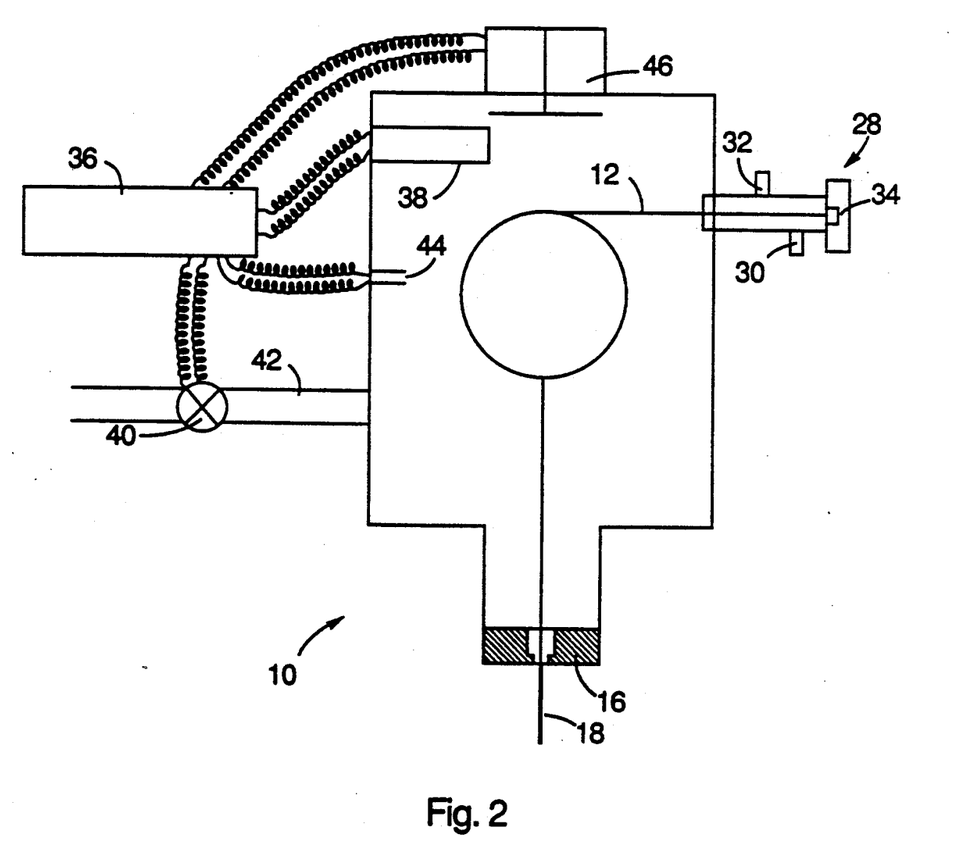
FIG. 2 is a more detailed schematic drawing of a temperature-controlled, thermally-isolated injector array for the apparatus made according to the present invention.

In FIG. 2, a more detailed schematic of the injector array 10 of the present invention is shown. A gas-tight on-column injector 28 having inlets for septum purge 30, introduction of a carrier gas 32, and introduction of the test sample 34 into the deactivated fused-silica pre-column 12, typically 1 to 5 meters long, is joined through a wall of the injector array oven 14 to the pre-column 12. A programmable controller 36 regulates a heater 38 inside the oven of the injector array 10 to provide heat for volatilizing the test sample within the pre-column 12. Also connected to the controller 36 are a solenoid valve 40 regulating flow of a fluid in a tube 42 connected between an external fluid source and the interior of the injector oven, a thermocouple 44 sensing the fluid temperature within the injector oven, and a fan 46 which maintains a fluid pressure in the injector array 10 greater than that in the adjacent gas chromatograph oven 14. This positive pressure of the cooling fluid enhances thermal isolation of the injector array from the heat generated by the gas chromatograph oven 14 during its temperature cycle operation. The design of the injector array 10 thus provides for volatilization, transport and introduction of a test sample to the analytical column of the GC oven at a temperature no greater than required to volatilize each specific compound(s) in the sample. Thus any thermal or catalytic decomposition of the compound(s) to be analyzed is avoided. Additionally, operation of the injector oven at other than sustained high temperatures as with conventional injector systems prevents activation of the deactivated fused-silica pre-column and subsequent adsorption/recombination interactions between the compound(s) to be analyzed and the pre-column. For example, the acid compound of EPA Method 625 can be transported to the analytical column by the pre-column 12 within the injector array 10 at temperatures less than 115° C.

Figure 3:
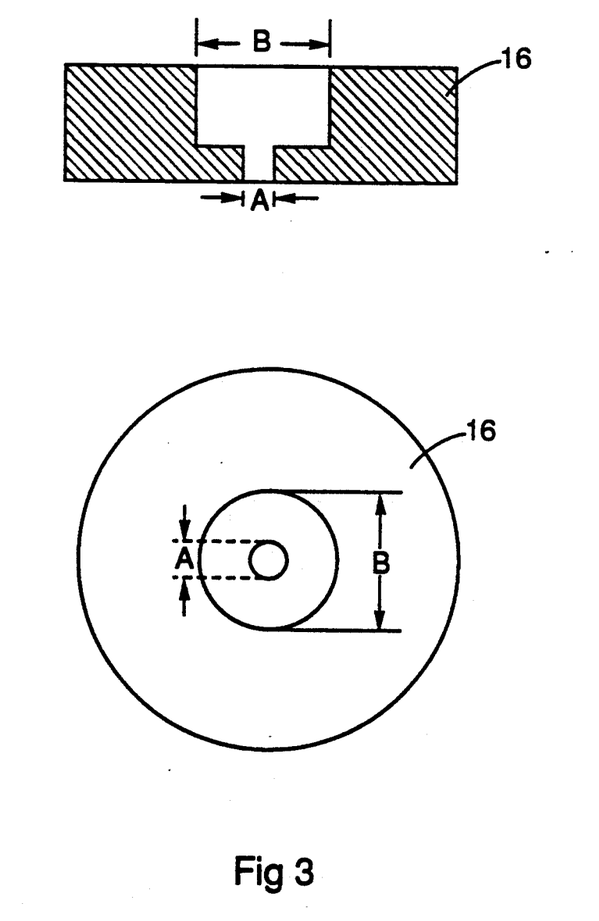
FIG. 3 is a schematic drawing for a thermally isolating interface plate used in an apparatus made according to the present invention.

FIG. 3 is a schematic of one of the interface plate 16 designed to thermally isolate the GC oven 14 from the on-column injector array 10. Interface plate 20 is similar in construction. Hole B is of large enough diameter to allow fluid flow to maintain the deactivated fused-silica pre-column 12 inside the injector array 10 and the deactivated fused-silica column 48 within the interface array 22 at the volatilization temperature of the compound(s) under analysis. The fluid pressure inside the injector array 10 and the interface array 22 is maintained greater than that inside the GC oven 14 so that there is no heated fluid flow from the GC oven 14 through Hole A into either the injector array 10 or the interface array 22. The interface plates 16, 20 are fabricated from material having good thermal insulation properties such as a ceramic, for example.

Figure 4:
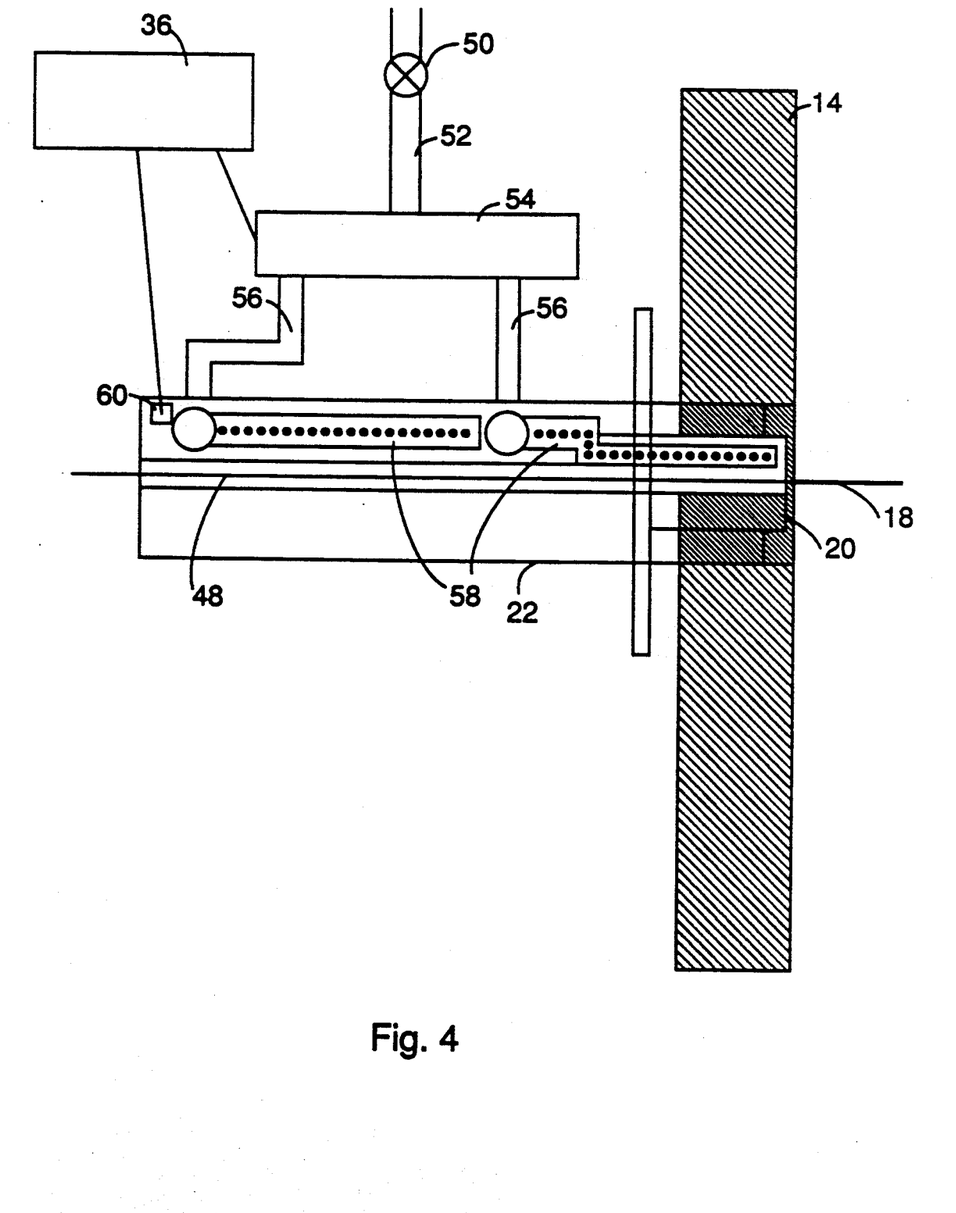
FIG. 4 is a more detailed schematic drawing of a thermally isolating interface array between said gas chromatograph and said mass spectrometer made according to the present invention.

The interface array 22 for the GC/MS system of the present invention is shown schematically in greater detail in FIG. 4. The interface array 22 is coupled to the GC oven 14 by thermal insulator plate 20 in the wall of the oven. The analytical column 18, carrying the separated compounds of the test sample from the GC oven, connects to a second section of deactivated fused-silica column 48 within the interface array 22 near the surface of the insulator plate 20 exterior to the GC oven. The second section of the deactivated fused-silica column transports the separated components of the sample under analysis to the ionization chamber 26 of the mass spectrometer 24.

Precise temperature control of the interface array 22 to enhance thermal isolation from the GC oven 14 is achieved by connecting the programmable controller 36 to a second solenoid valve 50 connecting the external fluid source to the interior of a heater block 54, which is also connected to the programmable controller 36. The fluid is transported from heater block 54 through an array of transfer tubes 56 to a fluid distribution tube 58 extending from within interface plate 20 along the longitudinal axis of the interface array 22. The programmable controller senses the temperature of the fluid interior to the array by means of a second thermocouple 60 and additionally maintains a positive pressure of the fluid inside the array with respect to that of the GC oven 14. For example, the acid compounds of EPA Method 625 can be transported by the interface from the GC column to the mass spectrometer at an interface temperature of 60° C.

Figure 5:
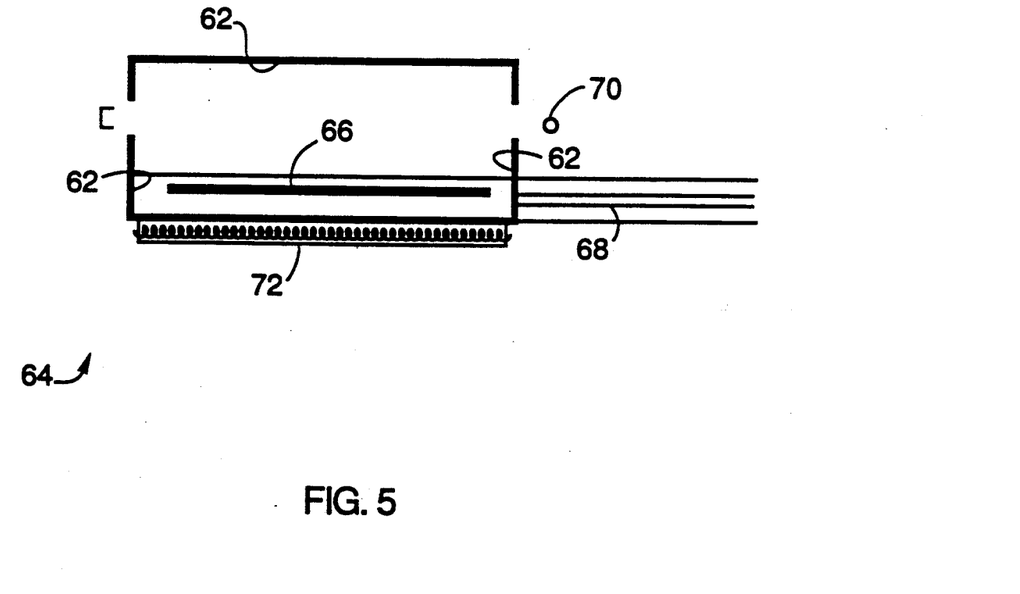
FIG. 5 is a schematic of an inert, temperature-controlled ionization chamber made according to the present invention for use in a mass spectrometer.

The ionization chamber 26 of the mass spectrometer 24 is shown schematically in FIG. 5.

The inner surface of a conventional stainless steel ionization chamber is coated with a nonreactive material, stainless steel for example, to deactivate it. However, this deactivated status is not maintained in the operation of conventional systems because the components of stainless steel, especially nickel, become highly reactive when subjected to high temperatures of normal operation, for example, operating temperatures about the range of 250° C. to 310° C. For the GC/MS system of the present invention, the inner surfaces 62 of the ionization chamber 64 and the ion repeller 66 interior to the chamber are plated with gold to a thickness of approximately 0.003 inches. After the plating operation, the gold surfaces are slightly active. Subsequently, the gold surfaces are ultrasonically cleaned in a solution of liquid detergent containing phosphoric acid, and then rinsed in an ultrasonically agitated bath of distilled water. Finally, the gold surfaces are rinsed with a silicating agent and dried at a temperature of 40° C. to produce a deactivated surface. Even with this deactivation treatment, the ionization chamber 64, if operated conventionally at 300° C., would reactivate in a few hours. In accordance with the present invention, however, it is determined that the ion source can be operated at a much lower temperature than that of conventional systems since the volatilized compounds in the analytical column within the GC will remain in the gaseous stage at these lower temperatures. This results from the ionization chamber 24 being operated at a vacuum of $10^{-5}$ torr. As an example, all compounds of EPA method 625 can be analyzed with a source temperature of less than 80° C. Also, the ionization chamber 24 does not become contaminated at these low temperature operations as conventional chambers do at high temperature operations. Consequently, the ionization chamber 64 operated according to the teachings of the present invention remains deactivated and non-contaminated for extended periods of time, as opposed to conventional ionization chambers which require frequent cleaning and maintenance. A cooling coil 68 circulating cooling fluid from the external source and regulated by the programmable controller 36 is added to the ionization chamber 26 of the present invention to precisely control the temperature of the chamber since electron filaments 70 will increase the temperature of the ionization chamber above 80° C., even with the heating apparatus 72 in the off condition. Also, the cooling coil 68 can be used for lowering the temperature of the ion source when data is not being collected.

Operation of the GC/MS system according to the teachings of the present invention is given below. In normal standby conditions, the injector array 10, the interface array 22 and ionization chamber 26 are at room temperature while the GC oven 14 is at a temperature of approximately 30° C. After the simultaneous start of data acquisition and injection of the test sample into the injector array 10, the temperature of the injector array 10 is held at room temperature for 30 seconds, then ramped to the maximum temperature in 5 minutes. The maximum temperature of the injector array is the volatilization temperature specific to the compound or class of compounds being separated and measured. For EPA method analysis, the temperature of the injector array 10 does not have to exceed 130° C. At the end of the 5 minute temperature ramp, the cooling fluid solenoid 40 is opened; and the injector array 10 system is rapidly cooled back to room temperature where it remains for the completion of the analysis. Following the injection sequence, the mass spectrometer 24 is placed in the data acquisition mode and the temperature of the ionization chamber 26 is brought up to the volatilization temperature of the compound(s) under test. The temperature of the GC oven 14 is ramped from 30° C. to 310° C. at 10° to 15° C. per minute. The interface array 22 temperature is controlled by the programmable controller 36 to exactly follow the temperature of the GC oven 14 up to the volatilization temperature of the compound(s) under test (below 80° C.). Temperature of the interface array 22 is then maintained at this temperature by controller 36 throughout the remainder of the analysis while the temperature of the GC oven 14 is increased by the controller 36 to 310° C. At the end of the data acquisition sequence, the temperature of the ionization chamber 26 and the interface array 22 are decreased by the controller 36 to room temperature. The temperature of GC oven 14 is cooled by controller 36 to 30° C. When all the standby temperatures have been obtained, the GC/MS system goes into the standby mode and is ready for analysis of the next sample.

An empirical comparison of sample testing between a conventional GC/MS system and the GC/MS system that is the subject of the present invention was run using a standard solution of phenols of EPA Method 625.

The standard solution of phenols was analyzed using the conventional system, and the analysis repeated after 1 day had elapsed. The results of the analyses are listed in Table 1.

An identical standard solution of phenols was analyzed using the GC/MS system of the present invention, and the analyses repeated after 14 days had elapsed. The results of these analyses are listed in Table 2.

In comparing the analyses, a significant difference was noted between the analyses of the conventional system after only 1 day had elapsed. Conversely, an insignificant difference was noted between analyses of the GC/MS system of the present invention even after 14 days had elapsed.

The data for the experiments indicate that the conventional system becomes activated very rapidly, as is indicated by the large decrease in the response factor for each of the phenols of the standard solution. The large change in response factors would disqualify the conventional system from performing the example EPA methods on the second day without recalibration of the system.

The GC/MS system of the present invention permits analysis of samples of reactive compounds without subjecting the samples to high operating temperatures and chemically active sites within the sample transport columns which cause erroneous results. Further, the GC/MS system of the present invention permits operation for extended periods of time analyzing reactive organic compounds while still remaining in compliance with required operating parameters and standards such as those of the U.S. Environmental Protection Agency. Picogram quantities of reactive organic compounds can be repetitively, accurately and economically measured in samples of materials.

TABLE 1

TIME EFFECTS ON PHENOL RESPONSE USING CONVENTIONAL GC/MS SYSTEM (1 Day)

| Compound | m/z | 100 ng | 100 ng |
|---|---|---|---|
| 1,4-Dichlorobenzene-D4 | 152 | I.S. | I.S. |
| Phenol | 66 | .350 | .290 |
| 2-Chlorophenol | 130 | .251 | .224 |
| Naphthalene-D8 | 137 | I.S. | I.S. |
| 2-Nitrophenol | 139 | .334 | .195 |
| 2,4-Dimethylphenol | 77 | .554 | .462 |
| 2,4-Dichlorophenol | 164 | .845 | .752 |
| Acenaphthene-D10 | 164 | I.S. | I.S. |
| 4-Chloro-3-Methylphenol | 77 | .145 | .127 |
| 2,4,6-Trichlorophenol | 196 | .166 | .134 |
| 4-Nitrophenol | 65 | .067 | .037 |
| Phenanthrene-D10 | 189 | I.S. | I.S. |
| 2-Methyl-4,6-Dinitrophenol | 198 | .059 | .047 |
| Pentachlorophenol | 266 | .372 | .255 |
| 2,4-Dinitrophenol | 184 | .031 | .019 |

Initials Conditions
1. Cold-On-Column Injection
2. GC Oven: 45-300° C., 10° C./Minute Operating Temperature
3. Interface Operating Temperature 300° C.
4. Ionization Chamber Operating Temperature 300° C.
5. Analytical Column: Supelco SPB-5, I.D.O.32, 30 Meter, 0.25 μm df

TABLE 2

TIME EFFECTS WITH GC/MS SYSTEM OF THE PRESENT INVENTION (14 Days)

| Compound | m/z | 100 ng | 100 ng |
|---|---|---|---|
| 1,4-Dichlorobenzene-D4 | 152 | I.S. | I.S. |
| Phenol | 66 | .182 | .226 |
| 2-Chlorophenol | 130 | .338 | .367 |
| Naphthalene-D8 | 137 | I.S. | I.S. |
| 2-Nitrophenol | 139 | 1.55 | 1.44 |
| 2,4-Dimethylphenol | 77 | .338 | .378 |
| 2,4-Dichlorophenol | 164 | 1.40 | 1.36 |
| Acenaphthene-D10 | 164 | I.S. | I.S. |
| 4-Chloro-3-Methylphenol | 77 | .071 | .084 |
| 2,4,6-Trichlorophenol | 196 | .248 | .262 |
| 4-Nitrophenol | 65 | .055 | .058 |
| Phenanthrene-D10 | 189 | I.S. | I.S. |
| 2-Methyl-4,6-Dinitrophenol | 198 | .342 | .440 |
| Pentachlorophenol | 266 | .705 | .728 |
| 2,4-Dinitrophenol | 184 | .315 | .304 |

Initials Conditions
* 1. New Prototype Cold-On-Column Injection System
* 2. New Prototype Interface Array
3. Analytical Column Restek, Rt$_x$-5, 30 Meter, 1.0 μm df, 0.32 mm I.D.

What is claimed is:

1. An apparatus for detecting and measuring a particular molecular compound in a sample under analysis containing a plurality of molecular compounds, said apparatus comprising:
   (a) a gas chromatograph for separating all said molecular compounds in said sample under analysis;
   (b) an injector array for introducing said test sample as volatilized molecular compounds into said gas chromatograph;
   (c) an interface array for receiving and transporting said volatilized and separated molecular compounds from said gas chromatograph into an ionization chamber of a mass spectrometer; and
   (d) a temperature control means coupled to said injector array, said interface array and said ionization chamber to programmably operate said injector array, said interface array and said ionization chamber at a volatilization temperature specific to said particular molecular compound.

2. The apparatus of claim 1 wherein said injector array is located external to said gas chromatograph.

3. The apparatus of claim 1 wherein said injector array is thermally isolated from said gas chromatograph by a first thermal insulator coupled between said injector array and said gas chromatograph.

4. The apparatus of claim 1 wherein said injector array further includes:
   (a) a first valve means for introducing a fluid from an external source into said injector array;
   (b) a first regulator means for sensing and regulating the temperature of said fluid, said first regulator means coupled to said temperature control means; and
   (c) a first pressure means for maintaining a first fluid pressure.

5. The apparatus of claim 1 wherein said fluid is a gas.

6. The apparatus of claim 1 wherein said first insulator is a machinable ceramic.

7. The apparatus of claim 1 wherein said interface array is thermally isolated from said gas chromatograph by a second thermal insulator coupled between said interface array and said gas chromatograph.

8. The apparatus of claim 1 wherein said interface array further includes:
   (a) a second valve means for introducing said fluid from said external source into said interface array;
   (b) a second regulator means for sensing and regulating the temperature of said fluid, said second regulator means coupled to said temperature control means; and
   (c) a second pressure means for maintaining a second fluid pressure inside said interface array.

9. The apparatus of claim 1 wherein said ionization chamber includes a repeller for deflecting ionized molecules, said repeller and all interior surfaces of said ionization chamber having chemically inert coatings.

10. The apparatus of claim 9 wherein said chemically inert coatings are composed of silicated gold, said coatings having a thickness of approximately 0.003 inches.

11. The apparatus of claim 1 wherein said ionization chamber includes:
   (a) a fluidic cooling means coupled to said external source for transporting said fluid about said ionization chamber; and
   (b) a third regulator means for sensing and regulating the temperature of said fluid, said third regulator means coupled to said temperature control means.

12. The apparatus of claim 11 wherein said fluidic cooling means is a fluid conducting coil surrounding said ionization chamber.

13. A gas chromatograph/mass spectrometer (GC/MS) apparatus for detecting a particular molecular compound contained among a plurality of molecular compounds, said apparatus comprising:
   (a) means for introducing a test sample containing said plurality of compounds into said GC/MS;
   (b) an interface array coupling said gas chromatograph of said apparatus to said mass spectrometer of said apparatus, said interface array transporting said plurality of molecular compounds in volatilized form to an ionization chamber of said mass spectrometer of said system; and
   (c) a programmable controller coupled to said GC/MS apparatus, said introducing means, said interface array and said ionization chamber such that said gas chromatograph is cycled through a predetermined temperature range, said introducing means, said interface array and said ionization chamber being operated at a selected volatilization temperature specific to said particular molecular compound.

14. The apparatus of claim 13 wherein said introducing means is an injector array located external to said gas chromatograph.

15. The apparatus of claim 14 wherein said injector array is thermally isolated from said gas chromatograph by a first thermal insulator coupled between said injector array and said gas chromatograph.

16. The apparatus of claim 14 wherein said injector array further includes:
   (a) a first valve means for introducing a fluid from an external source into said injector array;
   (b) a first regulator means for sensing and regulating the temperature of said fluid, said first regulator means coupled to said temperature control means; and
   (c) a first pressure means for maintaining a first fluid pressure.

17. The apparatus of claim 16 wherein said fluid is a gas.

18. The apparatus of claim 15 wherein said first thermal insulator is a machinable ceramic.

19. The apparatus of claim 13 wherein said interface array is thermally isolated from said gas chromatograph by a second thermal insulator coupled between said interface array and said gas chromatograph.

20. The apparatus of claim 13 wherein said interface array further includes:
   (a) a second valve means for introducing said fluid from said external source into said interface array;
   (b) a second regulator means for sensing and regulating the temperature of said fluid, said second regulator means coupled to said temperature control means; and 21. The apparatus of claim 13 wherein said ionization chamber includes a repeller for deflecting ionized molecules, said repeller and all interior surfaces of said ionization chamber having chemically inert coatings.

22. The apparatus of claim 21 wherein said chemically inert coatings are composed of silicated gold, said coatings having a thickness of approximately 0.003 inches.

23. The apparatus of claim 13 wherein said ionization chamber includes:
   (a) a fluidic cooling means coupled to said external source for transporting said fluid about said ionization chamber; and
   (b) a third regulator means for sensing and regulating the temperature of said fluid, said third regulator means coupled to said temperature control means.

24. The apparatus of claim 23 wherein said fluidic cooling means is a fluid conducting coil surrounding said ionization chamber.

25. A method for operating a gas chromatograph/mass spectrometer (GC/MS) system for separation and measurement of a singular molecular compound contained in a sample under analysis, said method comprising the steps of:
   (a) introducing said test sample into said GC/MS system;
   (b) operating an oven contained within said gas chromatograph within a selected temperature range necessary to separate all volatilized molecular compounds contained within said sample under analysis; and
   (c) programmably operating all elements of said GC/MS external to said oven at a volatilization temperature specific to said singular molecular compound.

26. A method of operating a gas chromatograph/mass spectrometer (GC/MS) system for separation and measurement of a particular molecular compound, said method comprising the steps of:
   (a) introducing a sample under analysis containing said particular molecular compound into a column in an injector array coupled to said gas chromatograph;
   (b) programmably controlling heating of said sample under analysis within said column in said injector array to a volatilization temperature specific to said singular molecular compound;
   (c) thermally isolating said injector array from an oven contained in said gas chromatograph;
   (d) introducing said test sample from said column in said injector array into an analytical column in said oven of said gas chromatograph;
   (e) programmably operating said oven of said gas chromatograph according to a selected time versus temperature profile to separate all molecular compounds within said sample under analysis;
   (f) transmitting said volatilized and separated compounds to an inert ionization chamber of said mass spectrometer via an interface array thermally isolating said gas chromatograph from said mass spectrometer;
   (g) programmably maintaining said interface array and said ionization chamber at said volatilization temperature specific to said particular molecular compound; and
   (h) measuring a mass to charge ratios specific to said particular compound with said mass spectrometer.

27. The method of claim 26 wherein said step of thermally isolating said injector array includes controlling flow of a fluid at a regulated temperature from an external source through said injector.

28. The method of claim 26 wherein said step of maintaining said interface array at said volatilization temperature includes controlling flow of said fluid at said regulated temperature from said external source through said interface array.

29. The method of claim 26 wherein said step of maintaining said ionization chamber at said volatilization temperature includes controlling flow of said fluid at said regulated temperature about said ionization chamber.

30. The method of claim 27 wherein said fluid is a gas.

* * * * *